United States Patent [19]
Woods et al.

[11] Patent Number: 5,230,119
[45] Date of Patent: Jul. 27, 1993

[54] MULTILAYER LAMINATED PAD

[75] Inventors: Marilyn S. Woods; James M. Woods, both of Escondido, Calif.

[73] Assignee: M. J. Woods, Inc., Grand Rapids, Mich.

[21] Appl. No.: 954,688

[22] Filed: Sep. 30, 1992

Related U.S. Application Data

[63] Continuation of Ser. No. 684,593, Apr. 12, 1991, abandoned, which is a continuation-in-part of Ser. No. 508,967, Apr. 13, 1990, abandoned.

[51] Int. Cl.$^5$ .......................... A47K 7/02; A61E 13/00
[52] U.S. Cl. .................................. 15/209.1; 15/104.94; 15/143.1; 128/917; 602/41; 602/58; 604/358; 604/385.1
[58] Field of Search ............. 15/104.94, 209.1, 229.13, 15/229.14, 210.1, 244.1, 244.3, 194, 143.1; 128/155, 851, 888, 917, 849; 132/293, 294; 401/130, 266; 604/289, 310, 358, 365, 367, 374, 377, 378, 385.1, 386; 602/41, 58

[56] References Cited

U.S. PATENT DOCUMENTS

| | | |
|---|---|---|
| Re. 26,385 | 5/1968 | Gilchrist . |
| 1,957,016 | 9/1934 | Nassif . |
| 2,156,270 | 5/1939 | Smith . |
| 2,616,428 | 11/1952 | Magee .......................... 604/377 X |
| 2,629,890 | 3/1953 | Giovanna . |
| 2,841,811 | 7/1958 | Carroll ............................ 15/244.1 |
| 2,927,335 | 3/1960 | Hammond .................... 15/244.1 X |
| 2,961,677 | 11/1960 | Zeccnini . |
| 2,964,772 | 12/1960 | Crawford . |
| 2,975,453 | 3/1961 | Imhof ............................ 15/244.1 X |
| 3,104,915 | 9/1963 | Perkovich et al. . |
| 3,131,410 | 5/1964 | Anderson et al. ............ 15/244.1 |
| 3,142,855 | 8/1961 | Gilchrist . |
| 3,221,359 | 12/1965 | Moroni et al. ............... 401/130 |
| 3,369,267 | 2/1968 | Friedland et al. . |
| 3,638,270 | 2/1972 | Schlegal, Jr. et al. . |
| 3,694,845 | 10/1972 | Engelsher . |
| 3,737,939 | 6/1973 | Jones, Sr. . |
| 3,784,998 | 1/1974 | Jones, Sr. . |
| 3,843,991 | 10/1974 | Vallis . |
| 3,955,233 | 5/1976 | Nakamura ...................... 15/209 R |
| 4,053,242 | 10/1977 | Mast, Jr. . |
| 4,104,616 | 3/1977 | Mast, Jr. et al. . |
| 4,121,386 | 10/1978 | Perez .......................... 15/209 R X |
| 4,372,867 | 2/1983 | Taragos . |
| 4,506,404 | 3/1985 | Clay . |
| 4,701,168 | 10/1987 | Gammons ...................... 604/310 |
| 4,829,995 | 5/1989 | Metters ........................ 604/289 X |
| 4,893,956 | 1/1990 | Wojcik et al. . |
| 4,925,453 | 5/1990 | Kannankeril . |

FOREIGN PATENT DOCUMENTS

| | | |
|---|---|---|
| 607525 | 7/1926 | France . |
| 660938 | 7/1929 | France ........................ 132/293 |
| 582504 | 12/1976 | Switzerland . |
| 4609 | of 1915 | United Kingdom . |
| 6160 | 3/1916 | United Kingdom . |
| 1158412 | 7/1969 | United Kingdom . |

Primary Examiner—Harvey C. Hornsby
Assistant Examiner—Charles Cooley
Attorney, Agent, or Firm—Varnum, Riddering, Schmidt & Howlett

[57] ABSTRACT

A disposable hand held laminated pad suitable for the application or removal of liquids and other materials while shielding the hand of the user from the materials includes a base pad having a lower wiping surface and an upper attachment surface, a thin impervious shield portion coextensive with and attached to the upper attachment surface, and a thin handle secured at a lower edge to the impervious shield and extending upwardly therefrom for grasping between fingers of a hand for enabling use thereof without contacting the fingers with the material being applied or wiped. The impervious shield helps prevent contact between a user of the pad and a person on which the pad is being used.

9 Claims, 5 Drawing Sheets

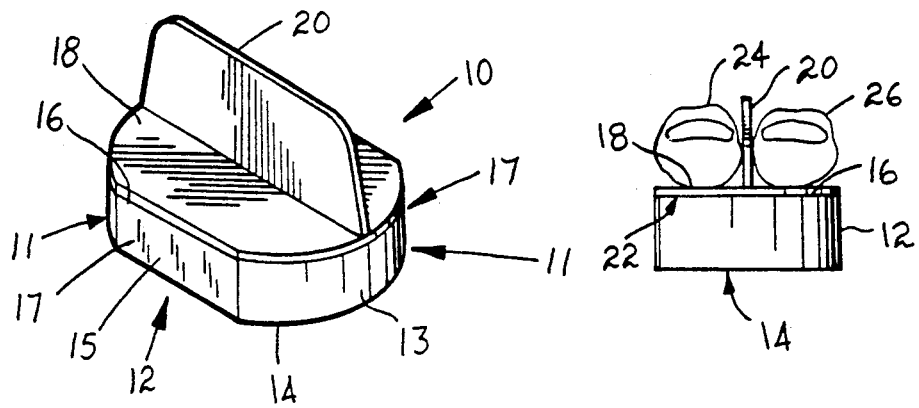
FIG. 1
FIG. 2
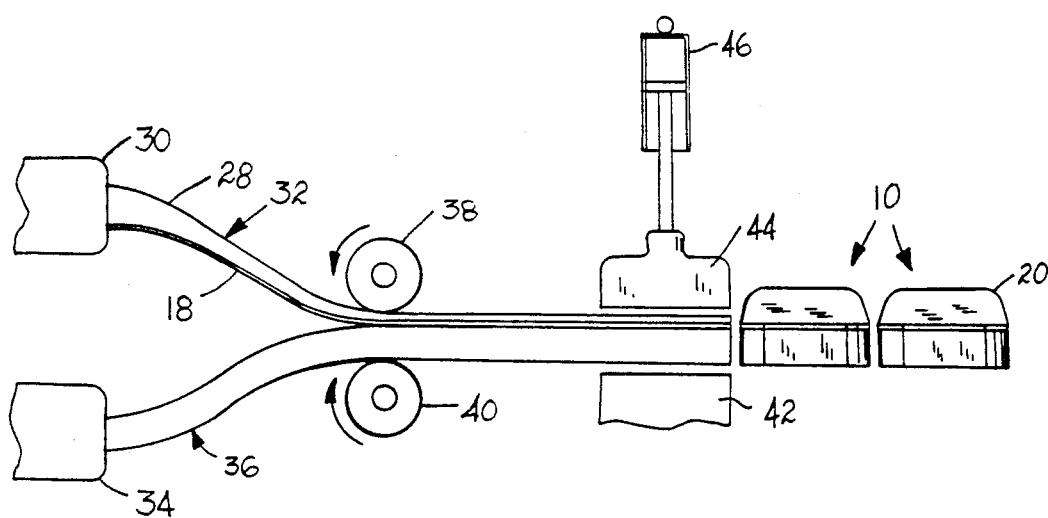
FIG. 3
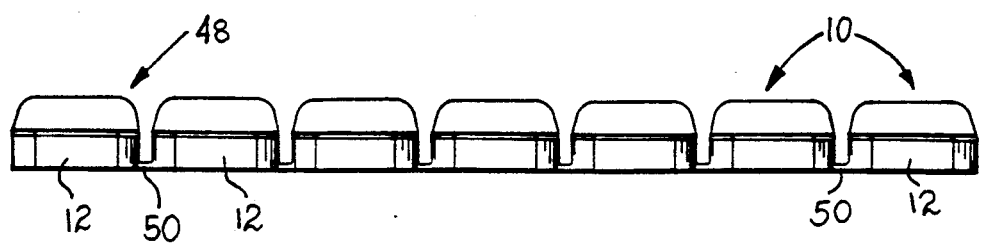
FIG. 4

MULTILAYER LAMINATED PAD

CROSS-REFERENCE TO RELATED APPLICATION

This is a continuation of application Ser. No. 07/684,593 filed Apr. 12, 1991 now abandoned, which is a continuation-in-part of U.S. application Ser. No. 07/508,967, filed on Apr. 13, 1990, now abandoned.

TECHNICAL FIELD

The present invention relates to a disposable multilayer laminated pad and a method of making the laminated pad. In particular, the present invention relates to an improved hand held laminated pad suitable as a wipe and/or applicator. The laminated pad has a non-woven base pad, an impervious barrier shield that protects the user from contact with fluids and solids on the base pad and a handle.

BACKGROUND OF THE INVENTION

Many items are widely used as wipes and applicators for wiping or applying substances from or to surfaces such as those on a human, e.g., skin, finger nails, toe nails, or in a human, e.g., internal organs and bones during an operation. Thus, these items are widely used in both medical and non-medical fields. Small cotton or rayon balls, pads or gauzes are perhaps the most widely used items for these purposes on the market today. Small sponges are also widely used items.

In the medical field, these items are used for cleaning the skin and other surfaces, such as the surfaces of internal organs, by the application of a disinfectant or solvent and/or the wiping away of blood and other fluids, including other body fluids, and other materials. The cotton balls, sponges and gauze pads are grasped between the fingers and applied to the area of concern to wipe away or apply fluids or other materials. One problem with this prior art approach is that the fingers frequently become contaminated with the fluid or other materials that can act as a conduit to transfer the contamination to other people or areas. This is especially a problem in view of the fluid borne diseases such as AIDS and hepatitis.

In the cosmetics and personal care fields, these items are widely used to apply and to remove makeup and to apply other personal care products such as lotions, creams and nail polish remover. Unfortunately, the item transfers the makeup or personal care product to the user's fingers which is often undesirable. For example, when a nail polish remover, which is usually acetone based, is being used it can be transferred to the fingers of the hand holding the item. The nail polish remover can harm the nails on the hand holding the item even if removal from these nails was not desired. Also, the nail polish remover can undesirably remove nail polish from a finger nail adjacent to the finger from which the nail polish is being removed. Also, the transfer can result in a waste of the makeup or personal care product.

These items are often amorphous in that they have no defined shape and therefore no defined edges. Thus, these items are not ideally suited to apply or wipe materials to or from surfaces that have an arcuate edge, e.g., finger nails, and from surfaces that have straight edge, e.g., the edge formed between the nose and cheek. Other items only have arcuate or straight edges and are not very effective when surfaces having a different shape are encountered.

One example of the prior art approach is disclosed in U.S. Pat. No. 4,053,242, entitled "Disposable Product Applicator and Dispensing Package Therefor", issued Oct. 11, 1977 to Mast, Jr. This patent discloses a combination of an applicator and a dispensing package wherein the applicator, described as a generally T-shaped disposable product applicator, with a pad portion of the applicator being capable of being folded upon itself which in folded condition lies flat and has a substantially uniform thickness so that it can be stacked in a dispensing container. When removed from the container, the pad portion of each applicator will automatically unfold and assume a product applying configuration. When the applicator pad portion is in its folded condition, the product application surface of the applicator is folded upon itself, and the product which is on or impregnated in the applying surface of the applicator will be protected from contamination.

Another example of applicators is illustrated in the Jones, Sr. U.S. Pat. No. 3,784,998, entitled "Composition Applicator", and its companion case U.S. Pat. No. 3,737,939 having substantially identical disclosures. These patents both disclose a pad, one of which is a sponge, the other of which is made of multiple sheets, both disclosed as having a generally hexagonal configuration, with a pair of coplanarly disposed applicator support sheets, both of which are slit, with the upper sheet being foldable to serve as a handle, and the second sheet to act as a shield sheet.

The Gilchrist U.S. Pat. No. Re. 26,385, issued May 7, 1968, discloses a liquid and paste applicator formed by sheets of foam, with a top sheet 26 foldable upward as shown in FIG. 2 to form a handle or hand grip.

The Clay U.S. Pat. No. 4,506,404 discloses a disposable sponge having a planar body portion and a pair of upstanding rib members spaced close enough that they may be grasped and squeezed against each other by the hand to form a handle or grip.

It is desirable to have an improved laminated pad suitable for use as an applicator or wipe that overcomes at least some of the aforementioned shortcomings.

SUMMARY OF THE INVENTION

The present invention is directed to a multilayer laminated pad suitable for use as an applicator or wipe. The laminated pad has a base pad, a pliable, impervious shield and an adjustable handle. The base pad has a substantially planar attachment surface and is nonwoven, soft, pliable and reversibly absorbent. The impervious shield has a top face and an opposed bottom face, the bottom face being affixed to the attachment surface. The shield is preferably coextensive with the base pad. The adjustable handle is affixed to the top face of the impervious shield.

A preferred laminated pad has edges of the base pad with each edge having a face that is preferably substantially perpendicular to the attachment surface. At least one of these edges is arcuate and at least one of these edges is straight. When the laminated pad is utilized to apply or wipe a material to or from a surface, such as a human body part, the edge of the laminated pad utilized can be selected to have a shape similar to that of the surface. Therefore, the laminated pad can be utilized to more accurately apply or remove a material from the surface without applying or removing material from an adjacent surface.

The material of the base pad is capable of absorbing material such as fluids and releasing the absorbed material under pressure. The requisite pressure to release absorbed material can be generated by forcing the base pad against the surface.

The impervious shield inhibits fluid and/or solid material on or in the base pad from migrating through the impervious shield to the fingers of the user. Thus, contacting of the material with the fingers is avoided. The shield preferably does not extend beyond the edges of the base pad unless additional shielding is desired. The shield also protects the user from fluid and/or solid material from another person.

The adjustable handle permits rotation of the base pad and impervious shield relative to the handle to permit the base pad to conform to the surface while permitting the user to maintain a comfortable grip on the handle.

The laminated pad is pliable and flexible which enables the laminated pad to conform to irregular surfaces and thus utilize the entire applying/wiping surface at the same time. The laminated pad can contain material to be applied to the surface. The base pad can be impregnated with a medicant, cosmetic, solvent or the like during the manufacturing of the laminated pad.

The present invention is also directed to a method of manufacturing the multilayer laminated pad that includes the steps of: providing a sheet-form base pad having a top attachment surface; providing a sheet-form, impervious shield having a bottom face and a top face; applying adhesive to at least one of the attachment surface or the bottom face; providing a handle-producing sheet having a bottom surface; selectably applying an adhesive to at least one of the top face or the bottom surface to cause partial adherence of the shield and handle-producing sheet upon combining the shield and handle-producing sheet; juxtaposing the top attachment surface and the bottom face to combine the base pad and the shield; and juxtaposing the top face and the bottom surface to combine the shield and the handle-producing sheet. The method can include the further step of cutting the combined base pad, shield and handle-producing sheet in the shape of the laminated pad and so that the handle-producing sheet has an adhered segment and a free segment. After the cutting step the free segment of the handle-producing sheet is available to be rotated and utilized as a handle.

BRIEF DESCRIPTION OF THE DRAWINGS

FIG. 1 is a perspective view of an embodiment of the laminated pad;

FIG. 2 is a front elevation view of the laminated pad of FIG. 1;

FIG. 3 is a schematic illustration of a method of manufacture of the laminated pad of FIG. 1;

FIG. 4 is a side elevation view of an array of laminated pads;

DETAILED DESCRIPTION OF A PREFERRED EMBODIMENT

Figure 5:
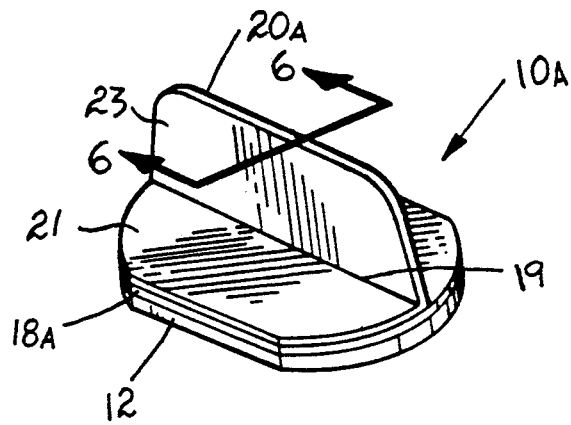
FIG. 5 is a perspective view of a preferred embodiment of the laminated pad.

Referring to the drawings, particularly to FIGS. 1 and 2, there is illustrated an embodiment of the laminated pad 10 of the present invention. The laminated pad 10 has a base pad member or portion 12 having a lower or applying/wiping surface 14 and an upper or top, generally parallel and planar attachment surface 16. The base pad 12 is an absorbent pad for absorbing a liquid or holding a material (such as solid powder), either for cleanup or for application of the liquid or material to a surface or the like.

The base pad 12 has at least one arcuate edge 11 having a face 13 that is substantially perpendicular to the attachment surface 16. The base pad 12 also has at least one straight edge 17 having a face 15 that is substantially perpendicular to the attachment surface 16. Most preferably, the base pad 12 has two opposed arcuate edges 11 and two opposed straight edges 17.

The base pad 12 is attached to a bottom face 22 of a fluid and solid impervious shield or barrier 18 and a handle or grasping tab 20, which can be in a generally T-shaped configuration with the shield or barrier 18 having attached thereto the upstanding handle 20.

Figure 6:
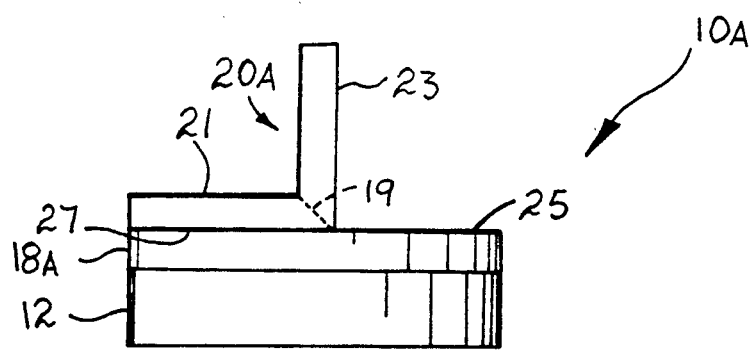
FIG. 6 is a front elevational view of the laminated pad of FIG. 5 taken along line 6—6.

As shown in FIGS. 5 and 6, the preferred laminated pad 10A has an impervious shield 18A that is coextensive with and affixed to the base pad 12. The handle 20A has a bottom surface 27 which is partially adhered to a top face 25 of the shield 18A to produce an adhered segment 21 and a free segment 23. Free segment 23 is capable of movement along a fold or score 19 to permit rotation of the handle 20A relative to the shield 18A and base pad 12.

The shield 18A is preferably pliable and impervious to the fluids and solids to which the base pad 12 is exposed.

The laminated pad is designed such that it may be conveniently made in various sizes, with one size as illustrated for ease of use in place of the typical cotton balls and the like. To this end, the applicator can be made of a size such that the handle extends upward a distance on the order of about one-half inch to about one inch to extend slightly above the typical or average size human fingers 24 and 26, as illustrated in FIG. 2. The laminated pad can have a width of about twice the height of the tab or handle (about one to about two inches) for a preferred size The laminated pad can have a length of slightly greater than its width This size of the laminated pad and handle provide an easy and convenient size, with a convenient way of grasping and manipulating the laminated pad between a pair of adjacent fingers, as illustrated. It can also be grasped between the thumb and forefinger or other finger of the hand. The shield or barrier panel protects the hand or fingers against contamination by a liquid or other material contained, absorbed, or contacted by the base pad. The present construction also lends itself to easy and economical construction for the production of simple and inexpensive laminated pads.

Referring to FIG. 3, there is illustrated a schematic diagram of a typical production process and method of making the laminated pads 10 of the present invention. A first extruder 30 extrudes a T-bar form of a member 32, which has an inverted T cross section and can be formed of a thin flexible plastic material, e.g., about 0.02 to 0.03 millimeters (mm). An adjacent and parallel extruder or dispenser 34 provides a continuous elongated member 36 of a suitable base pad material. The members 32 and 36 are fed through a pair of opposed rollers 38 and 40 that are rotated in the directions indicated by their respective arrows. The rollers 38 and 40 bring the two members 32 and 36 together at the mating surfaces and bond them into a combined, unitary structure. This unitary structure proceeds forward and passes over a back up mandrel or the like 42, above which is disposed a reciprocating cutter 44 powered by a suitable hydraulic or air cylinder 46 for cutting the combined structure into the laminated pads 10. The roller 38 biases a central leg 28 of the T-bar 32 downward in a planar position parallel to one side of the shield 18, and the cutter 44 simultaneously cuts the members 32 and 36 As the cutter 44 is removed, the handle 20 can pop or be rotated up. The laminated pads 10 may be totally separated, as illustrated in FIG. 3, into separate and distinct laminated pads 10 or may be formed as an array 48 of detachable laminated pads 10 as shown in FIG. 4. The mandrel 42 and cutter 44 are selected to achieve the desired results.

Referring to FIG. 4, a plurality of the laminated pads are formed in a manner similar to that shown in FIG. 3. However, base pads 12 remain connected together by a thin connector strip 50, such that the nest or array 48 of the laminated pads 10 may be rolled onto a roller or the like and dispensed by tearing off individual laminated pads. In an embodiment that is not illustrated, the array can have a number of rows and columns of laminated pads 10. Alternatively, a number of arrays 48 can be stacked and boxed in a nest-like fashion. A laminated pad is selected for use and the connector strip 50 is torn, separating the selected laminated pad from the adjacent laminated pad(s).

In an alternative embodiment that is not illustrated, the connector strip 50 is formed from the shield or handle.

Figure 7:
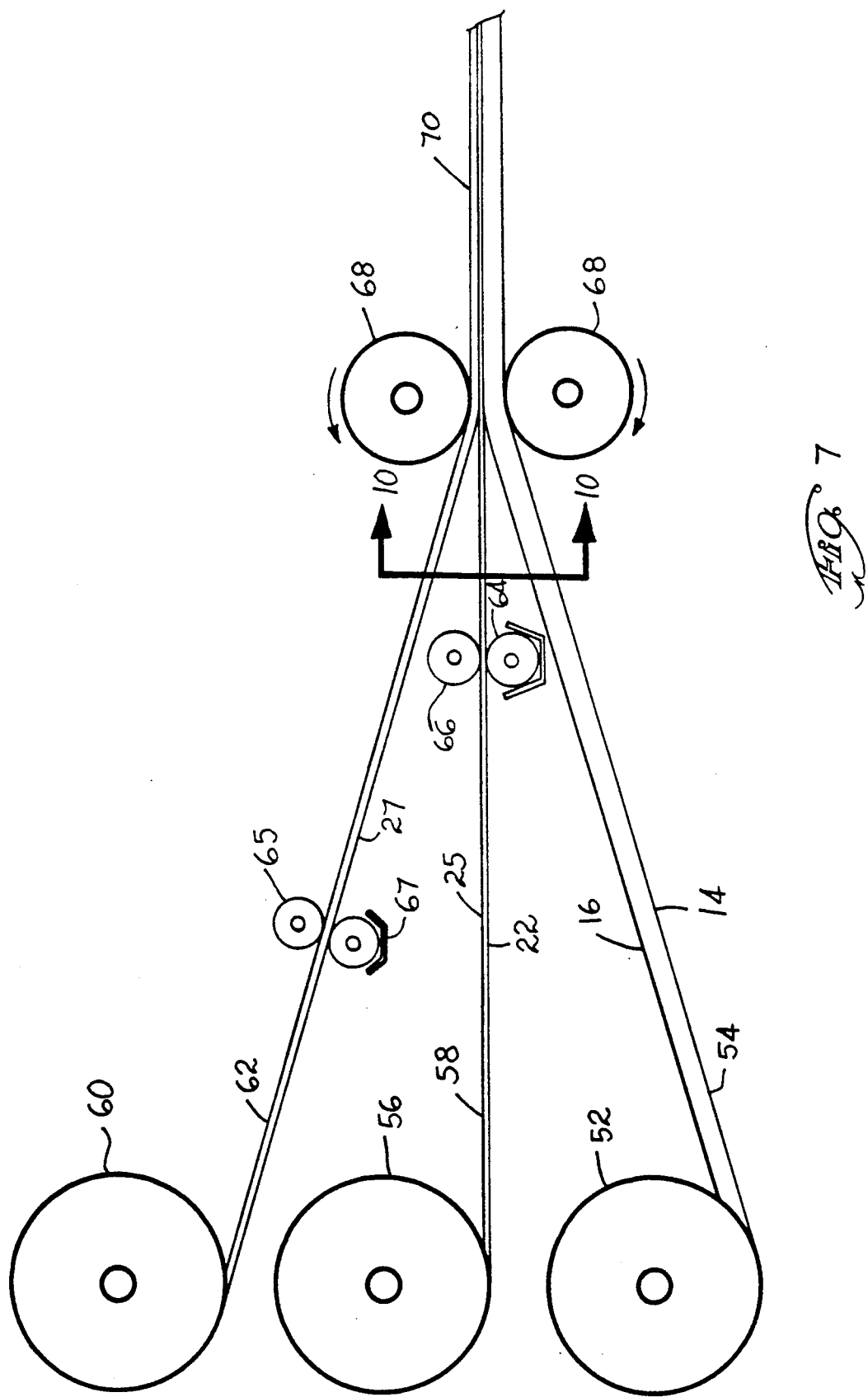
FIG. 7 is a schematic illustration of a preferred method of manufacturing the laminated pad of FIG. 5.

FIG. 7 illustrates a preferred method of producing the laminated pad of the present invention wherein the laminated pad has three layers. A roll 52 provides sheet-formed base pad material 54, a roll 56 provides sheet-form impervious shield material 58 and a roll 60 provides sheet-form handle-producing material 62. A conventional adhesive is coated onto the bottom face 22 of the impervious shield material 58 by a full surface adhesive coater 64. Alternatively, the adhesive can be coated onto the attachment surface 16 of the base pad material. This alternative embodiment is not illustrated. A conventional adhesive is selectively coated onto the top face 25 of the impervious shield material 58 in strips by a partial, adhesive strip-forming coater 66. Alternatively, the adhesive can be selectively coated onto the bottom surface 27 of the handle-producing material 62. This alternative embodiment is not illustrated. In further alternative embodiments, also not illustrated, adhesive is coated onto at least one of the attachment surface 16 and the bottom face 22 and adhesive is selectively coated to at least one of the top face 25 and the bottom surface 27. The materials 54, 58 and 60 are then forced between two opposed rollers 68 whose directions of rotation are indicated by their respective arrows. The rollers 68 provide sufficient compressive force to adhere the materials 54, 58 and 62 to each other and produce a laminated sheet 70. The laminated sheet can then be fed into a mandrel 42 and cutter 44 assembly as shown in FIG. 3 to produce laminated pads. As discussed above, the mandrel and cutter assembly can be selected to produce an array of laminated pads.

Optionally, the handle-producing material 60 can be scored either prior to or after passing between the rollers 68. Scoring can be achieved utilizing a scoring roller 65 and a compression roller 67.

Figure 8:
FIG. 8 is a side view of a coater for coating adhesive onto the shield.

FIG. 8 illustrates the full surface adhesive coater 64 as a roller that provides adhesive to the entire bottom face or attachment surface.

Figure 9:
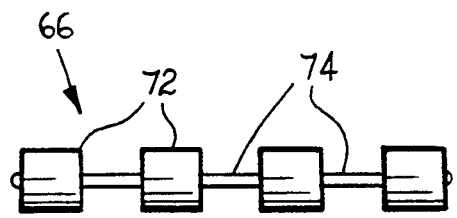
FIG. 9 is a side view of a coater for selectively coating adhesive onto the handle-producing sheet.

FIG. 9 illustrates the partial, adhesive strip-forming coater 66 that selectively coats strips of adhesive to the top face or bottom surface. The strip-forming coater 66 has adhesive coating sections 72 with non-adhesive coating sections 74 therebetween.

Figure 10:
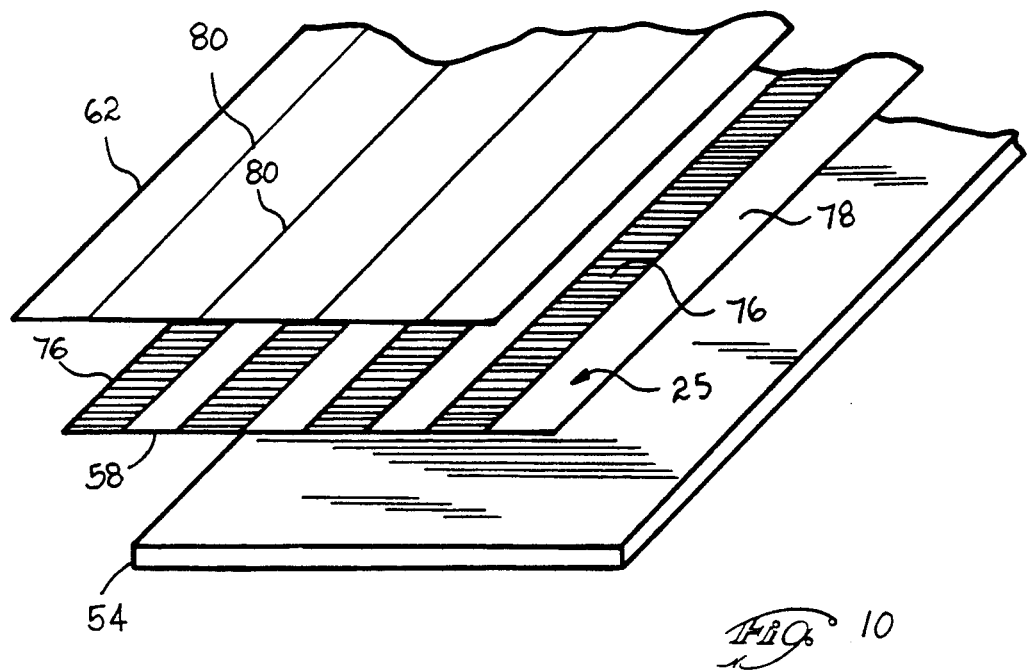
FIG. 10 is an exploded elevational view of the three sheets used to produce the laminated pad taken along line 10—10 of FIG. 7.

FIG. 10 illustrates the top face 25 of the impervious shield material 58 having adhesive coated sections 76 and uncoated sections 78. The handle-producing material 62 has score lines 80 which are positioned so that when the laminated sheet is cut the handle can be more readily rotated into the desired position.

Figure 11:
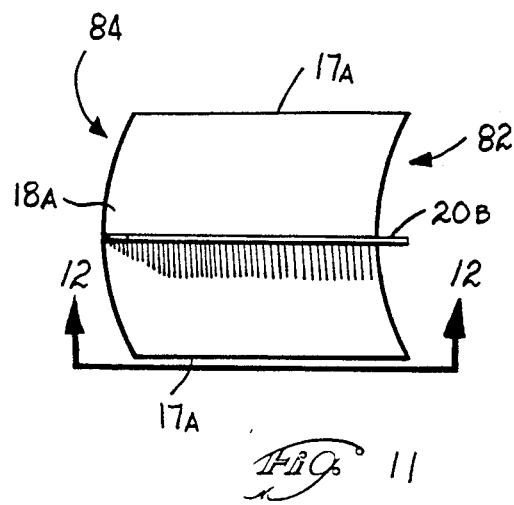
FIG. 11 is a top elevational view of an alternative embodiment of the laminated pad.
Figure 12:
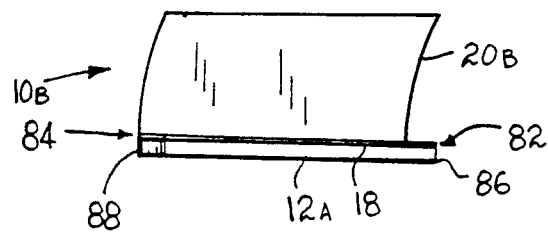
FIG. 12 is a side elevational view of the laminated pad of FIG. 11 taken along line 12—12 of FIG. 11.

FIGS. 11 and 12 illustrate an alternative embodiment of the laminated pad 10B. The laminated pad 10B has a base pad 12A and a concave arcuate edge 82 and a convex arcuate edge 84. The base pad 12A also has a face 86 of the concave arcuate edge 82 and a face 88 of the convex arcuate edge 84. The concave arcuate edge 82 and face 86 can be utilized on surfaces that have a convex end (not shown). The convex arcuate edge 84 and face 88 can be used on a surface having a concave end (not shown). The laminated pad 10B also has straight edges 17A that are utilized as described above.

Figure 13:
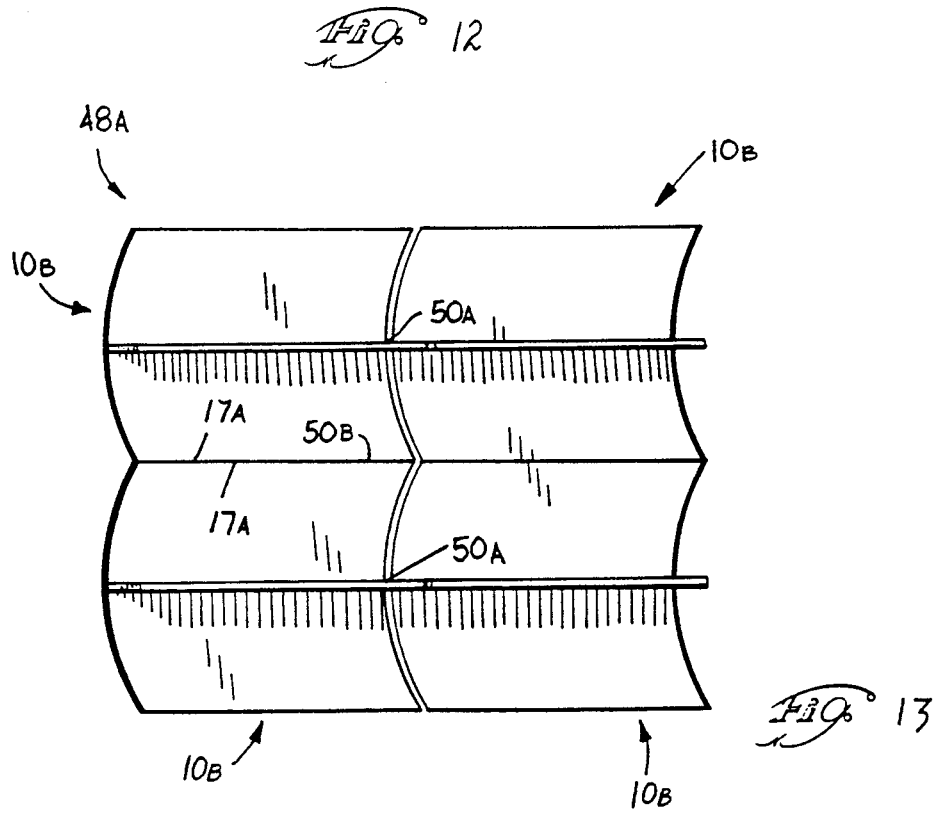
FIG. 13 is a top elevational view of an array of laminated pads.

FIG. 13 illustrates an array 48A of four laminated pads 10B, it being understood that the number of laminated pads in the array 48A is not limited to four and the array 48A can be symmetrical or unsymmetrical. Connector strips 50A and 50B extend between adjacent laminated pads 10B to maintain the array 48A. Connector strip 50B can be a separable line of demarcation between the straight edges 17A of the laminated pads 10B. The connector strips 50A and 50B permit individual laminated pads 10B to be detached from the array 48A.

The base pad can be made of any number of foam compositions, a woven or non-woven fiber or fabric material, gauze, sponge, and the like. Preferably, the base pad is made of a non-woven material that is soft, pliable and reversibly absorbent. More preferably, the base pad is made of a material that is substantially lintless. The preferred material for the base pad is capable of holding a fluid or solid material and subsequently releasing the fluid or solid material by the application of pressure. The base pad is most preferably made of a conventional entangled cotton which is typically processed with water to cause entanglement of the cotton fibers. A commercially available entangled cotton is Webril from International Paper Co., Veratec Division, Walpole, Mass.

The handle and shield can be made of the same material that can be any suitable impervious, non-reactant material, such as a treated paper that is impervious or a suitable thin plastic film material. The material preferably is flexible and has structural integrity, such that it can be easily handled and support its structure and the base pad.

The shield preferably has a thickness on the order of about 0.02 to 0.03 mm.

Preferably, the material that the shield and handle are made of is non-reactive with materials to be applied or removed or to be impregnated into the base pad. The laminated pad can also preferably be made with biodegradable materials.

Suitable materials for the impervious shield include paper impregnated or coated with a latex or resin to render the paper impervious, sheet-form plastic, e.g., polyethylene and polypropylene, and the like. The handle can be made of the same material as the shield provided that the material has enough strength to enable the user to properly grip the handle and apply the desired force to the laminated pad.

Suitable bonding between the shield or barrier and base pad can be achieved with a non-reactive bonding. This may be accomplished by mechanical bonding between the materials, such as electromagnetic, and other forms or adhesives may be utilized.

The adhesive utilized to produce the laminated sheet that is cut into laminated pads can be a conventional adhesive that provides sufficient bonding of the various layers of material and which is substantially non-reactive with, and does not degrade upon exposure to, the materials to which the laminated pad is exposed.

The laminated pad can be used for the application of various materials, such as liquids, pastes, powders and the like to various surfaces, and/or may be utilized for the removal of such materials. The laminated pad can be impregnated with a material to be applied. The laminated pad has many uses, including nail polish removal by the application of acetone and other solvents and the like. It may also be utilized for application and/or removal of facial and other skin cleansers, moisturizers, makeup, etc. It can also be used in the medical field, either for the application of various medications or the like, or for cleansing and the like. The pad can be sterilized for medical use.

While we have illustrated and described our invention by means of specific embodiments, it is to be understood that numerous changes and modifications may be made therein without departing from the spirit and scope of the invention as defined the appended claims.

We claim:

1. An applicator/wipe pad for applying a liquid or solid substance and for removing a liquid or solid substance by wiping comprising:
    a reversibly absorbent pad having an applying/wiping surface, an attachment surface, the attachment surface being disposed opposite the applying/wiping surface and having edges defining an outer periphery;
    a flexible continuous shield member having a lower surface, an upper surface, and edges defining an outer periphery, the lower surface of the shield member being mounted to the attachment surface of the pad and the outer periphery of the shield member being at least coextensive with the outer periphery of the pad; and
    a flexible L-shaped handle consisting of first and second legs each of which is connected along a single straight fold line and having edges defining an outer periphery, the outer periphery of the shield member being substantially coextensive with the outer periphery of the handle, the first leg of the handle being permanently affixed along its entirety to the upper surface of the shield member and the second leg of the handle being pivotally mounted to the first leg such that the second leg can be rotated from a first position wherein said first and second legs lie in a single plane, to a second position which is substantially normal to the applying/wiping surface or any orientation in between the first and second positions;
    whereby a user grasps the second leg of the L-shaped handle in the second position to apply or wipe a solid or liquid substance with the applicator/wipe pad and the shield member prevents contact of the user with the substance being applied or wiped and the surface being applied or wiped.

2. An applicator/wipe pad according to claim 1 wherein the pad has four edges, two edges being arcuate and two edges being straight.

3. An applicator/wipe pad according to claim 2 wherein one of the two arcuate edges is a concave arcuate edge and the other of the two arcuate edges is a convex arcuate edge.

4. An applicator/wipe pad according to claim 1 wherein the pad comprises 100% entangled cotton.

5. An applicator/wipe pad according to claim 1 wherein the pad comprises a non-woven fiber.

6. An applicator/wipe pad according to claim 1 wherein the flexible continuous shield member comprises a thin plastic film.

7. An applicator/wipe pad according to claim 6 wherein the thin plastic film is selected from the group comprising polyethylene and polypropylene.

8. An applicator/wipe pad according to claim 1 wherein the flexible L-shaped handle comprises a thin plastic film.

9. An applicator/wipe pad according to claim 8 wherein the thin plastic film is selected from the group comprising polyethylene and polypropylene.

* * * * *